US011860133B1

(12) United States Patent
Zhang et al.

(10) Patent No.: US 11,860,133 B1
(45) Date of Patent: Jan. 2, 2024

(54) MULTI-SHAFT PRESSURIZED ROCK MECHANICS TESTER

(71) Applicant: Chengdu University of Technology, Chengdu (CN)

(72) Inventors: Chen Zhang, Chengdu (CN); Huaguo Wen, Chengdu (CN); Chao Ma, Chengdu (CN); Yiquan Ma, Chengdu (CN); Jintong Liang, Chengdu (CN); Yixin Dong, Chengdu (CN); Xiangye Kong, Chengdu (CN); Xin Wang, Chengdu (CN); Shaohui Wang, Chengdu (CN); Ya Zhang, Chengdu (CN); Wei Yan, Chengdu (CN)

(73) Assignee: Chengdu University of Technology, Chengdu (CN)

( * ) Notice: Subject to any disclaimer, the term of this patent is extended or adjusted under 35 U.S.C. 154(b) by 0 days.

(21) Appl. No.: 18/358,868

(22) Filed: Jul. 25, 2023

(30) Foreign Application Priority Data

Jun. 20, 2022 (CN) ........................ 202210694159.2

(51) Int. Cl.

| | |
|---|---|
| ***G01N 3/04*** | (2006.01) |
| ***G01N 33/24*** | (2006.01) |
| ***G01N 3/10*** | (2006.01) |

(52) U.S. Cl.
CPC ................ *G01N 3/04* (2013.01); *G01N 3/10* (2013.01); *G01N 33/24* (2013.01); *G01N 2203/0048* (2013.01)

(58) Field of Classification Search
CPC ........... G01N 3/10; G01N 3/04; G01N 33/24; G01N 2203/0048
See application file for complete search history.

(56) References Cited

U.S. PATENT DOCUMENTS

2009/0084168 A1* 4/2009 Bulled .................... G01N 3/40 73/78

FOREIGN PATENT DOCUMENTS

| | | |
|---|---|---|
| CN | 209182158 U | 7/2019 |
| CN | 211094696 U | 7/2020 |
| CN | 214539018 U | 10/2021 |

* cited by examiner

*Primary Examiner* — Jonathan M Dunlap
(74) *Attorney, Agent, or Firm* — Nitin Kaushik

(57) ABSTRACT

Disclosed is a multi-shaft pressurized rock mechanics tester, pertaining to the technical field of rock mechanics testing devices, comprising a base; the base is of an integral rectangular structure, and welded six vertical support plates symmetrically at the front and back ends, a 日 -shaped bracket plate is horizontally welded at the top of the six vertical support plates ("日 " is a Chinese character, read as "Ri"), and a bracket plate is rotatably installed on the top section of the three rear vertical support plates, pressed against the 日 -shaped bracket plate; the left and right sides of the base are symmetrically welded with four vertical bracing plates, an I-shaped installation plate is welded on the top of the four vertical bracing plates, four hydraulic cylinders are locked, fixed and hoisted on the bottom of the I-shaped installation plate with screws.

6 Claims, 9 Drawing Sheets

MULTI-SHAFT PRESSURIZED ROCK MECHANICS TESTER

CROSS-REFERENCE TO RELATED APPLICATIONS

The application claims priority to Chinese patent application No. 2022106941592, filed on Jun. 20, 2022, the entire contents of which are incorporated herein by reference.

TECHNICAL FIELD

The present invention pertains to the technical field of rock mechanics testing devices, in particular to a multi-shaft pressurized rock mechanics tester.

BACKGROUND

Rock mechanics is a branch of mechanics, with a research purpose of solving the rock engineering problems in the construction of water conservancy and civil works, etc. The principal test method is to forcefully crash the rock by top pressing with multiple jacking shafts (piston rods of oil cylinders). The post-test rock fragment unloading mechanism on the existing rock mechanics tester is not reasonably designed, and it is necessary to be pushed, scraped and cleaned manually with the help of external tools, which is troublesome, laborious and inconvenient. Although some unloading mechanism can be overturned without the assistance of external tools, additional manual labor is required for overturning during operation, which is cumbersome and time-consuming.

SUMMARY

The invention aims to provide a multi-shaft pressurized rock mechanics tester which has two gear racks for power transmission. When being lowered, shrunk and hidden after the test is completed, the fence frame can slide downward with interference and interlinked and engaged to drive two driven gears to control the bracket plate to overturn and unload the materials, which solves the problem of a troublesome and time-consuming operation, that is, driving the bracket plate to overturn with the help of additional manual effort.

In order to achieve the above objectives, the present invention provides the following technical solutions: a multi-shaft pressurized rock mechanics tester, comprising a base; the base is of an integral rectangular structure, and welded six vertical support plates symmetrically at the front and back ends, a 日 -shaped bracket plate is horizontally welded at the top of the six vertical support plates ("日 " is a Chinese character, read as "Ri"), and a bracket plate is rotatably installed on the top section of the three rear vertical support plates, pressed against the 日 -shaped bracket plate, and used to support the rock to be tested; the left and right sides of the base are symmetrically welded with four vertical bracing plates, an I-shaped installation plate is welded on the top of the four vertical bracing plates, four hydraulic cylinders are locked, fixed and hoisted on the bottom of the I-shaped installation plate with screws, a square press plate is locked, fixed and hoisted at the bottom of four piston shafts on the four hydraulic cylinders with screws, and a jacking pillar is welded and fixed at the bottom center of the square press plate and slides down to contact the rock block to be tested; two of four vertical strip grooves are set respectively on the front and back ends of the vertical support plates (101), a positioning shaft is welded in each of the four vertical strip grooves, and a rectangular fence frame is mounted on the four positioning shafts in a sliding way; two six-edge positioning shaft are symmetrically welded on the middle section of the front and back vertical support plates located in the middle position, two L-shaped inserts are installed on the two six-edge positioning shafts by pushing and sliding a first set of spring on the top; two 凵 -shaped foot frames ("凵 " a Chinese character, read as "Kan") are symmetrically welded on the bottom of the left and right panels of the fence frame.

Preferably, a vertical short shaft is welded to the middle section of the horizontal brace connecting rod located on the left side inside the base, and a stepping frame is mounted on the vertical short shaft in a sliding way.

Preferably, a rotating shaft is welded at the rear of the bracket plate and two driven gears are symmetrically sleeved on the left and right ends of the rotating shaft.

Preferably, two gear racks are symmetrically welded in both sides on the top of the rear panel of fence frame and will get engaged and contacted with the two driven gears while the fence frame slides down with interference.

Preferably, the four F-shaped sliding bars are symmetrically welded at the bottom of the front and rear panels of the fence frame, and four sliding sleeves are welded at the bottom of the four F-shaped sliding bars, and the four sliding sleeves are pushed by a second set of springs to slide with the four positioning shafts.

Preferably, the head ends of the two L-shaped inserts (6) both have an oblique section structure, two protruding support rods are welded in opposite directions on the vertical support sections of the two L-shaped inserts, and the tails of the two protruding support rods are rotatably connected to two connecting rods.

Preferably, the two wedges are symmetrically welded on the inner side of the middle section of the front and rear panels of fence frame and will slide down and come into contact with the oblique sections of the head ends of the two L-shaped inserts.

Preferably, the stepping frame has a rectangular rear with opening structure, and the tails of the two side support shafts of the stepping frame are rotatably connected together with the tails of the two connecting rods.

Compared with the prior art, the invention has the following beneficial effects:

1. As the bracket plate in the invention is rotatably connected, it can be turned up and set in an inclined state after the test is completed to unload the rock slag, which saves the trouble of manually pushing, scraping and unloading the rock slag with the help of external tools, making the cleaning and unloading at the top of the bracket plate convenient and quick;

2. Two gear racks are provided in the invention for power transmission; when being lowered, shrunk and hidden after the test is completed, the fence frame can slide downward with interference and interlinked and engaged to drive two driven gears to control the bracket plate to overturn and unload the materials, which solves the problem of driving the bracket plate to overturn with the help additional manual effort, which is convenient to operation, saving both time and labor;

3. In the invention, two L-shaped inserts can be inserted to position two wedges and limit the fence frame to a sliding idle state, but the fence frame can still continue to slide downward with interference after being blocked by two L-shaped inserts, which ensures the fence frame is interlinked to overturn the bracket plate normally;

4. In the invention, two connecting rods, two L-shaped inserts and a stepping frame are connected together to form a double-crank sliding bar mechanism, through which the stepping frame can be driven by foot to slide downward to extract and release the two L-shaped inserts, saving the trouble of bending over and holding the stepping frame compared with manual operation.

Figure 1:
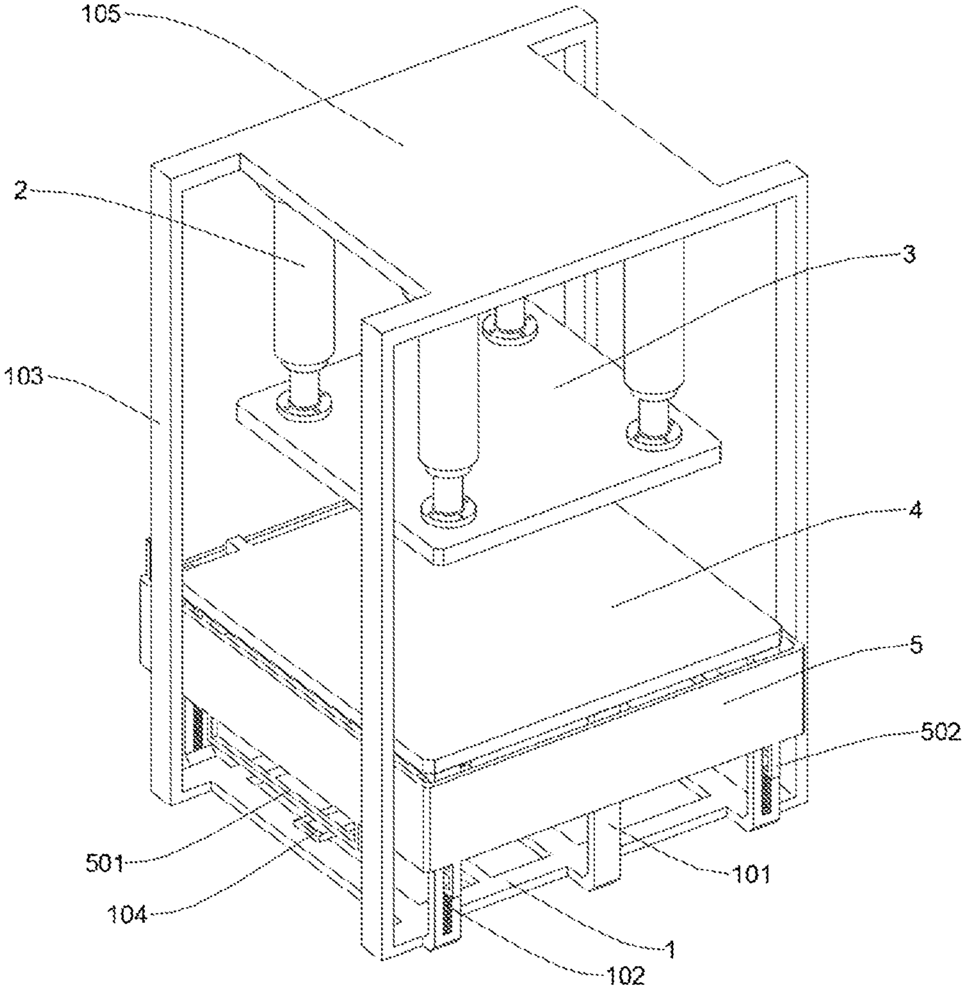
FIG. 1 is a schematic diagram of the overall structure of the invention.
Figure 2:
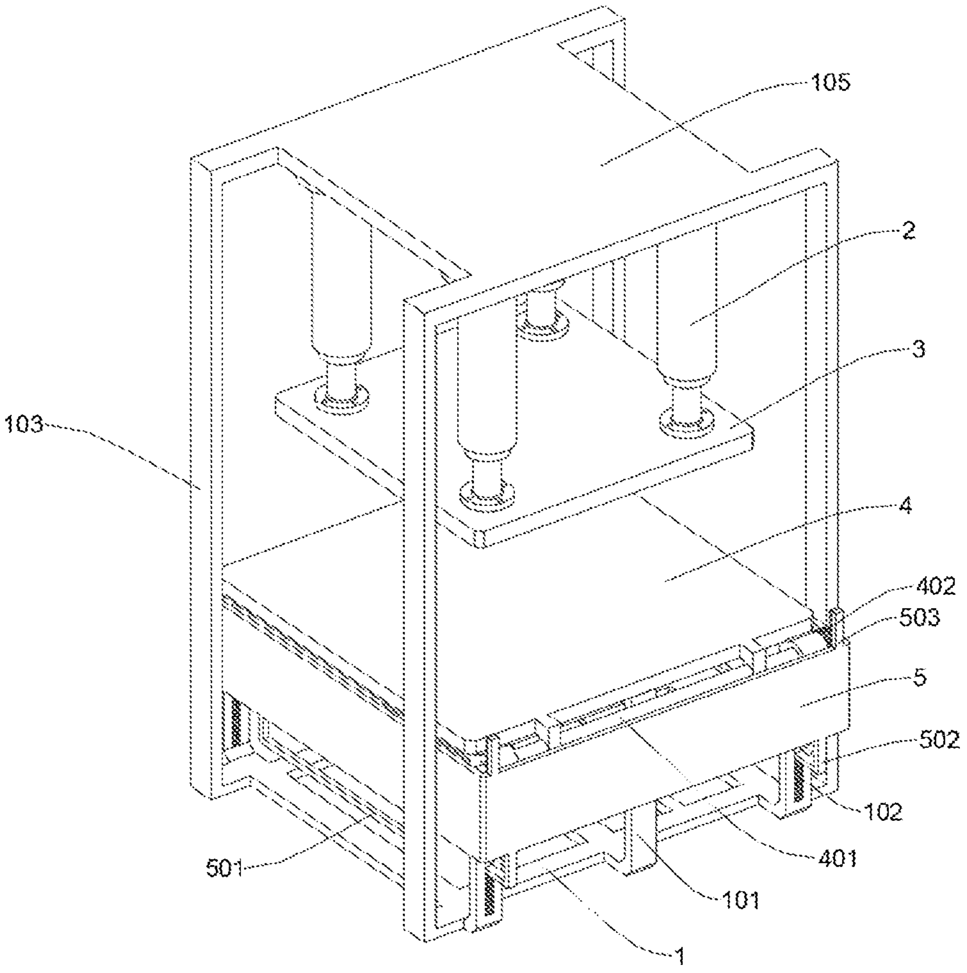
FIG. 2 is a schematic diagram of the overall rear structure of the invention.

1. Base; 101. Vertical support plate; 102. Positioning shaft; 103. Vertical bracing plate; 104. Stepping frame; 105. I-shaped installation plate; 106. Six-edge positioning shaft; 107. Vertical short shaft; 2. Hydraulic cylinder; 3. Square press plate; 301. Jacking pillar; 4. Bracket plate; 401. Rotating shaft; 402. Driven gear; 5. Fence frame; 501. Foot frame; 502. F-shaped sliding bar; 503. Gear rack; 504. Wedge; 6. L-shaped insert; 601. Connecting rod.

DETAILED DESCRIPTION OF THE EMBODIMENTS

The technical solutions of the embodiments of the present invention will be described expressly and integrally in conjunction with the appended figures of the embodiments of the present invention. It is clear that the described embodiments are some but not all of the embodiments of the present invention.

Referring to FIGS. 1 to 9, the invention presents an embodiment: a multi-shaft pressurized rock mechanics tester comprising a base (1), wherein the base (1) is of an integral rectangular structure, and welded six vertical support plates (101) symmetrically at the front and back ends, a 日 -shaped bracket plate is horizontally welded at the top of the six vertical support plates (101) ("凵" is a Chinese character, read as "Ri"), and a bracket plate (4) is rotatably installed on the top section of the three rear vertical support plates (101), pressed against the 日 -shaped bracket plate, and used to support the rock to be tested; the left and right sides of the base (1) are symmetrically welded with four vertical bracing plates (103), an I-shaped installation plate (105) is welded on the top of the four vertical bracing plates (103), four hydraulic cylinders (2) are locked, fixed and hoisted on the bottom of the I-shaped installation plate with screws, a square press plate (3) is locked, fixed and hoisted at the bottom of four piston shafts on the four hydraulic cylinders (2) with screws, and a jacking pillar (301) is welded and fixed at the bottom center of the square press plate (3) and slides down to contact the rock block to be tested; two of four vertical strip grooves are set respectively on the front and back ends of the vertical support plates (101), a positioning shaft (102) is welded in each of the four vertical strip grooves, and a rectangular fence frame (5) is mounted on the four positioning shafts (102) in a sliding way; two six-edge positioning shaft (106) are symmetrically welded on the middle section of the front and back vertical support plates (101) located in the middle position, two L-shaped inserts (6) are installed on the two six-edge positioning shafts (106) by pushing and sliding a first set of spring on the top, the four hydraulic cylinders (2) can push the square press plate (3) and the jacking pillar (301) down through the four piston shafts on the cylinders to test the rock mechanical properties, the fence flame (5) during the test can slide up to baffle the top of the bracket plate (4) to intercept the broken rocks to prevent the rocks from jumping and injuring people, and the fence flame (5) can slide down and hidden under the bottom of the bracket plate (4) before and after the test so as not to block the rocks or affect rock unloading; two 凵 -shaped foot frames (501) ("凵" a Chinese character, read as "Kan") are symmetrically welded on the bottom of the left and right panels of the fence frame (5) and used in conjunction with the springs on the four positioning shafts (102), the fence frame (5) can be driven by foot to slide up and down to switch between blocking and idle states, making it more labor-saving compared to manual operation; the four F-shaped sliding bars (502) are symmetrically welded at the bottom of the front and rear panels of the fence frame (5), and four sliding sleeves are welded at the bottom of the four F-shaped sliding bars (502), and the four sliding sleeves are pushed by a second set of springs to slide with the four positioning shafts (102); the head ends of the two L-shaped inserts (6) both have an oblique section structure, and two protruding support rods are welded in opposite directions on the vertical support sections of the two L-shaped inserts (6), and the tails of the two protruding support rods are rotatably connected to two connecting rods (601); a vertical short shaft (107) is welded to the middle section of the horizontal brace connecting rod located on the left side inside the base (1), and a stepping frame (104) is mounted on the vertical short shaft (107) in a sliding way.

Figure 6:
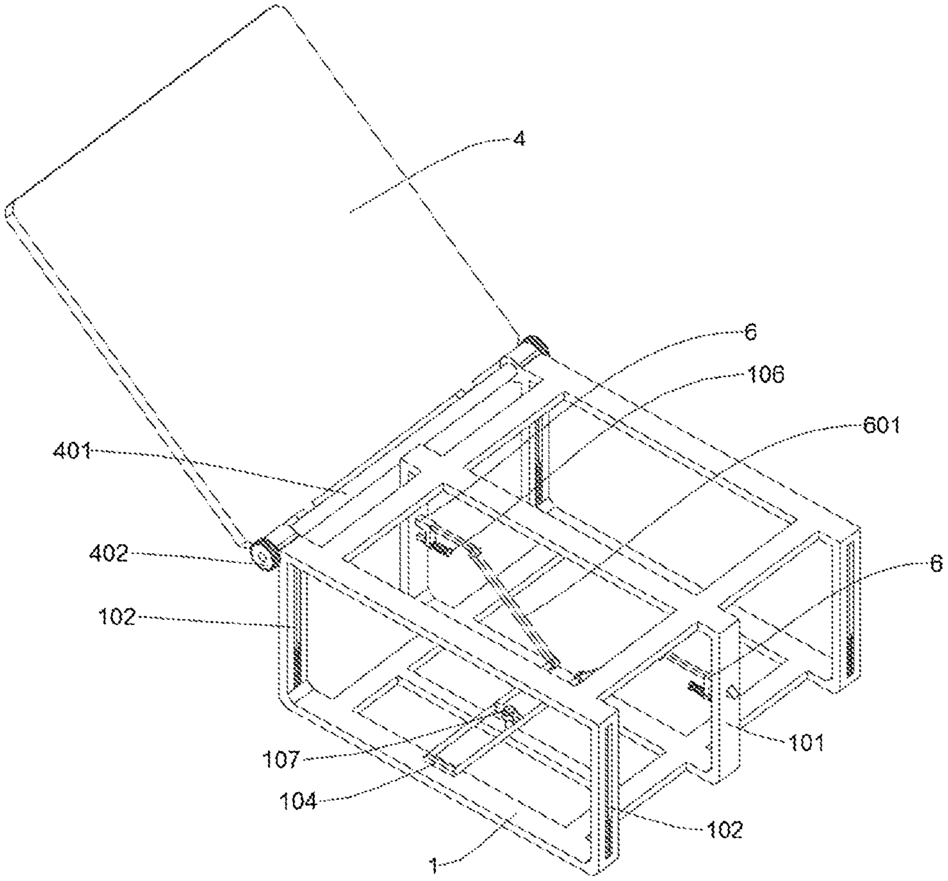
FIG. 6 is a schematic diagram of the installation position of L-shaped insert in the invention.
Figure 7:
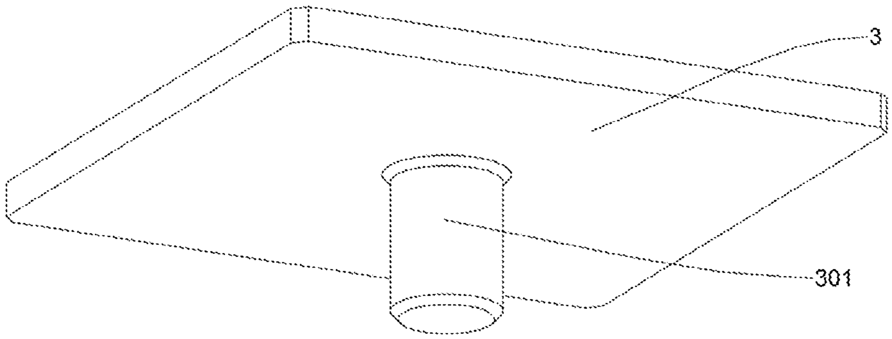
FIG. 7 is a schematic diagram of the bottom structure of square press plate in the invention.

As shown in FIG. 6, a rotating shaft (401) is welded at the rear of the bracket plate (4) and two driven gears (402) are symmetrically sleeved on the left and right ends of the rotating shaft (401); as the bracket plate (4) is rotatably connected, it can be turned up and set in an inclined state after the test is completed to unload the rock slag, which saves the trouble of manually pushing, scraping and unloading the rock slag with the help of external tools, making the cleaning and unloading at the top of the bracket plate (4) convenient and quick.

Figure 3:
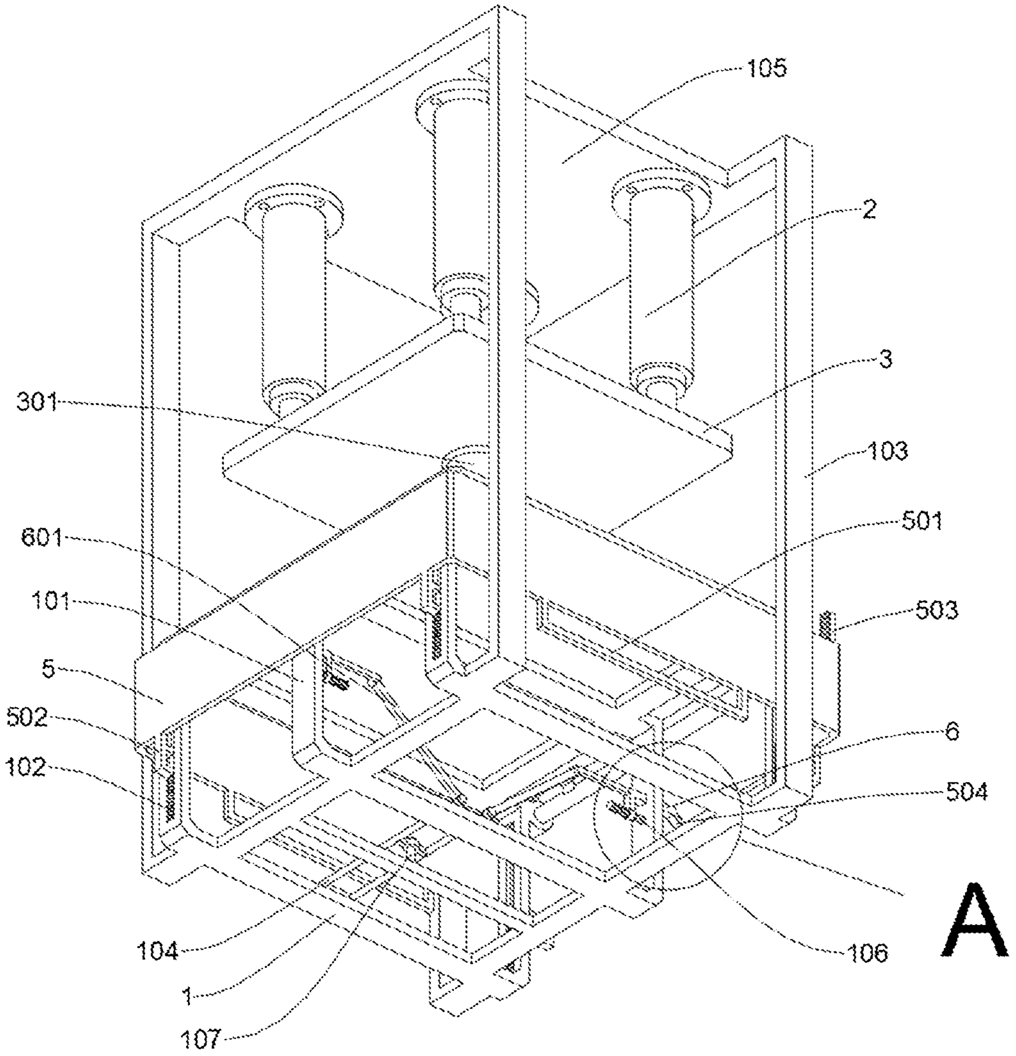
FIG. 3 is a schematic diagram of the overall bottom structure in the invention.
Figure 4:
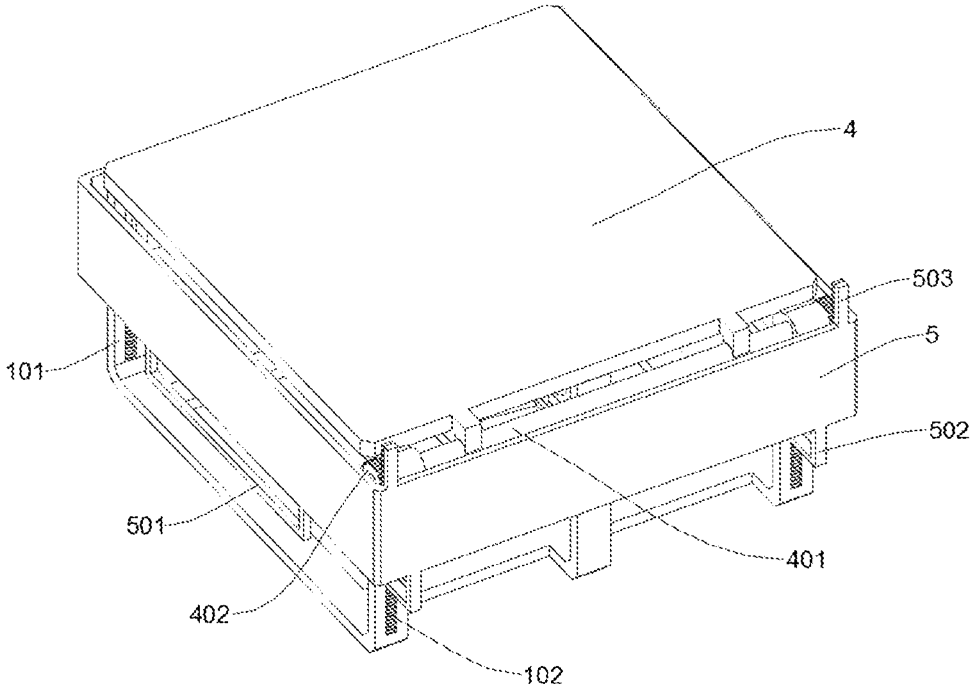
FIG. 4 is a schematic diagram of the bracket plate in horizontal state in the invention.
Figure 5:
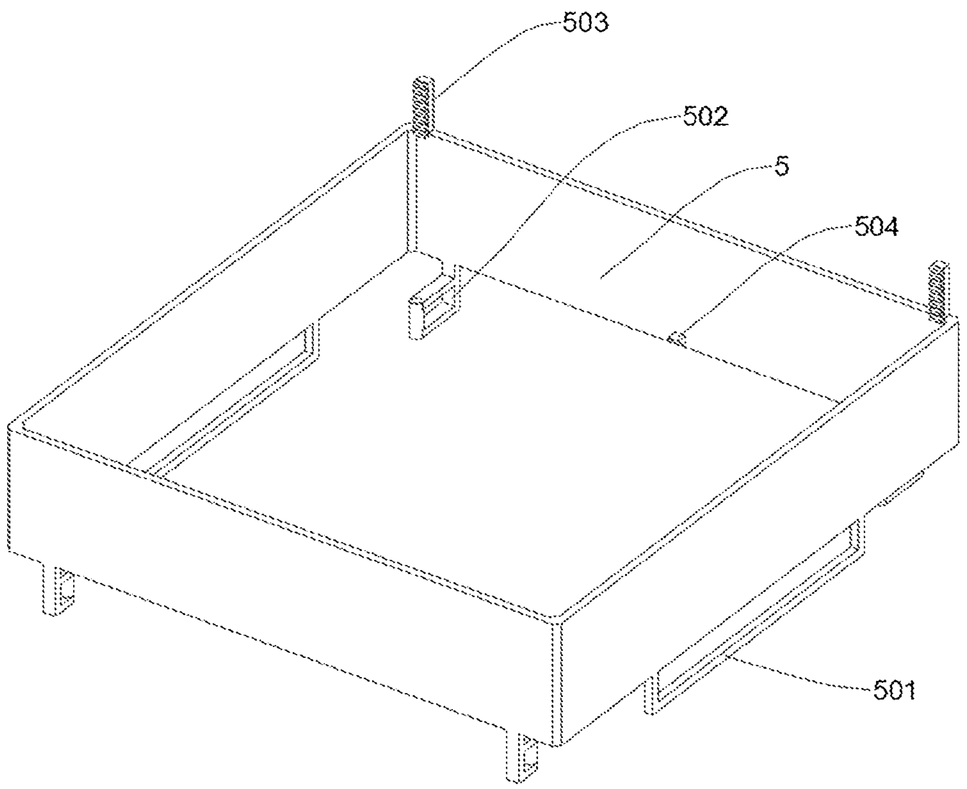
FIG. 5 is a schematic diagram of the fence frame structure in the invention.
Figure 8:
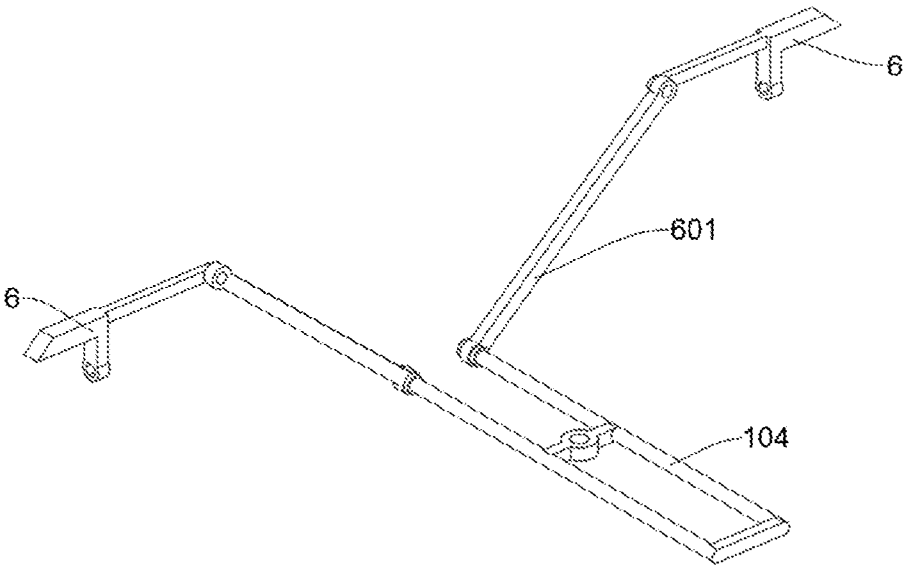
FIG. 8 is a schematic diagram of the stepping frame structure in the invention.
Figure 9:
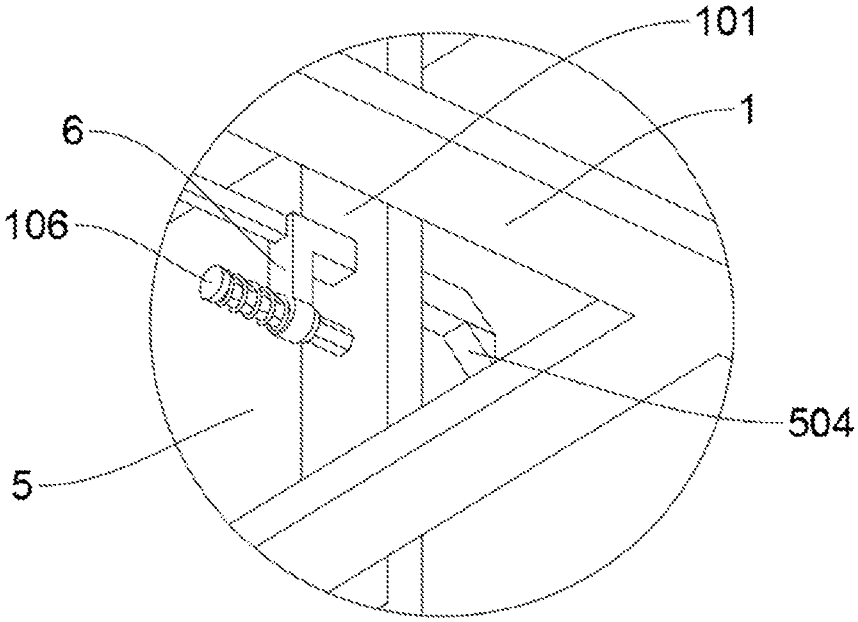
FIG. 9 is a schematic diagram of the enlarged structure of Part A in FIG. 1 in the invention.

As shown in FIG. 4, two gear racks (503) are symmetrically welded in both sides on the top of the rear panel of fence frame (5) and will get engaged and contacted with the two driven gears (402) while the fence frame (5) slides down with interference; through the power transmission by the two racks (503), when being lowered, shrunk and hidden after the test is completed, the fence frame (5) can slide downward with interference and interlinked and engaged to drive the two driven gears (402) to control the bracket plate (4) to overturn and unload the materials, which solves the problem of driving the bracket plate (4) to overturn with the help additional manual effort, which is convenient to operation, saving both time and labor;

As shown in FIG. 3, two wedges (504) are symmetrically welded on the inner side of the middle section of the front and rear panels of fence frame (5) and will slide down and come into contact with the oblique sections of the head ends of the two L-shaped inserts (6), and the two L-shaped inserts (6) can be inserted to position two wedges (504) and limit the fence frame (5) to a sliding idle state, but the fence frame (5) can still continue to slide downward with interference after being blocked by the two L-shaped inserts (6), which ensures the fence frame (5) is interlinked to overturn the bracket plate (4) normally;

As shown in FIG. 8, the stepping frame (104) has a rectangular rear with opening structure, and the tails of the two side support shafts of the stepping frame (104) are rotatably connected together with the tails of the two connecting rods (601); two connecting rods (601), two L-shaped inserts (6) and a stepping frame (104) are connected together to form a double-crank sliding bar mechanism, through which the stepping frame (104) can be driven by foot to slide downward to extract and release the two L-shaped inserts (6), saving the trouble of bending over and holding the stepping frame (104) compared with manual operation.

Working principle: the rock to be tested is first placed in the top center position of the bracket plate (4), and the press frame (104) is driven by foot to slide down; since the two connecting rods (601), the two L-shaped inserts (6) and the stepping frame (104) are connected together to form a double-crank sliding bar mechanism, the stepping frame (104) can slide down to drive the two L-shaped inserts (6) to slide and release the fence frame (5); after being released positioning, the fence frame (5) is jacked by the spring on the four positioning shafts (102) and can slide up to baffle the top of the bracket plate (4), and then the four hydraulic cylinders (2) are started and push the square press plate (3) and the jacking pillar (301) downward through the four piston shafts on the cylinders to test the rock mechanical properties; after the test is completed, the square press plate (3) is lifted up by the four hydraulic cylinders (2), and finally the fence frame (5) is driven to slide down and hidden by the dynamic output of the foot frame (501); through the power transmission by the two racks (503), when being lowered, shrunk and hidden after the test is completed, the fence frame (5) can slide downward with interference and interlinked and engaged to drive the two driven gears (402) to control the bracket plate (4) to overturn and unload the materials; the inclined bracket plate (4) can be used to unload the rock slag on it, and can be driven back to its horizontal position when the fence frame is restored upward by sliding with interference, preparing for the next test.

It is apparent to those skilled in the art that the present invention is not limited to the details of the above exemplary embodiments, and that the present invention is capable of being realized in other specific forms without departing from the spirit or essential features of the present invention. Accordingly, the embodiments shall be regarded as exemplary and non-limiting in every point of view, and the scope of the present invention is limited by the appended claims and not by the foregoing specification, and is therefore intended to encompass all variations falling within the meaning and scope of the equivalent elements of the claims. Any appended markings in the claims shall not be regarded as a limitation to claims of the present invention.

What is claimed is:

1. A multi-shaft pressurized rock mechanics tester, comprising a base (1); the base (1) is of an integral rectangular structure, and welded six vertical support plates (101) symmetrically at the front and back ends, a 日 -shaped bracket plate is horizontally welded at the top of the six vertical support plates (101) (“日 ” is a Chinese character, read as “Ri”), and a bracket plate (4) is rotatably installed on the top section of the three rear vertical support plates (101), pressed against the 日 -shaped bracket plate, and used to support the rock to be tested; the left and right sides of the base (1) are symmetrically welded with four vertical bracing plates (103), an I-shaped installation plate (105) is welded on the top of the four vertical bracing plates (103), four hydraulic cylinders (2) are locked, fixed and hoisted on the bottom of the I-shaped installation plate with screws, a square press plate (3) is locked, fixed and hoisted at the bottom of four piston shafts on the four hydraulic cylinders (2) with screws, and a jacking pillar (301) is welded and fixed at the bottom center of the square press plate (3) and slides down to contact the rock block to be tested; two of four vertical strip grooves are set respectively on the front and back ends of the vertical support plates (101), a positioning shaft (102) is welded in each of the four vertical strip grooves, and a rectangular fence frame (5) is mounted on the four positioning shafts (102) in a sliding way; two six-edge positioning shaft (106) are symmetrically welded on the middle section of the front and back vertical support plates (101) located in the middle position, two L-shaped inserts (6) are installed on the two six-edge positioning shafts (106) by pushing and sliding a first set of spring on the top; two 凵 -shaped foot frames (501) (“凵 ” a Chinese character, read as “Kan”) are symmetrically welded on the bottom of the left and right panels of the fence frame (5); a rotating shaft (401) is welded at the rear of the bracket plate (4) and two driven gears (402) are symmetrically sleeved on the left and right ends of the rotating shaft (401); two gear racks (503) are symmetrically welded in both sides on the top of the rear panel of fence frame (5) and will get engaged and contacted with the two driven gears (402) while the fence frame (5) slides down with interference; four F-shaped sliding bars (502) are symmetrically welded at the bottom of the front and rear panels of the fence frame (5), and four sliding sleeves are welded at the bottom of the four F-shaped sliding bars (502), and the four sliding sleeves are pushed by a second set of springs to slide with the four positioning shafts (102).

2. The multi-shaft pressurized rock mechanics tester according to claim 1, wherein a vertical short shaft (107) is welded to the middle section of a horizontal brace connecting rod located on the left side inside the base (1), and a stepping frame (104) is mounted on the vertical short shaft (107) in a sliding way.

3. The multi-shaft pressurized rock mechanics tester according to claim 2, wherein the head ends of the two L-shaped inserts (6) both have an oblique section structure, and two protruding support rods are welded in opposite directions on the vertical support sections of the two L-shaped inserts (6).

4. The multi-shaft pressurized rock mechanics tester according to claim 3, wherein the tails of the two protruding support rods are rotatably connected to two connecting rods (601).

5. The multi-shaft pressurized rock mechanics tester according to claim 4, wherein the stepping frame (104) has a rectangular rear with opening structure, and the tails of a two side support shafts of the stepping frame (104) are rotatably connected together with the tails of the two connecting rods (601).

6. The multi-shaft pressurized rock mechanics tester according to claim 1, wherein two wedges (504) are symmetrically welded on the inner side of the middle section of the front and rear panels of fence frame (5) and will slide down and meet the oblique sections of the head ends of the two L-shaped inserts (6).

* * * * *